US006306917B1

(12) United States Patent
Bohn et al.

(10) Patent No.: US 6,306,917 B1
(45) Date of Patent: Oct. 23, 2001

(54) PROCESSES FOR THE PRODUCTION OF HYDROCARBONS, POWER AND CARBON DIOXIDE FROM CARBON-CONTAINING MATERIALS

(75) Inventors: Mark S. Bohn, Golden; Charles S. Benham, Littleton, both of CO (US)

(73) Assignee: Rentech, Inc., Denver, CO (US)

( * ) Notice: Subject to any disclaimer, the term of this patent is extended or adjusted under 35 U.S.C. 154(b) by 0 days.

(21) Appl. No.: 09/376,709

(22) Filed: Aug. 17, 1999

Related U.S. Application Data (63) Continuation-in-part of application No. 09/212,374, filed on Dec. 16, 1998, now abandoned.

(51) Int. Cl.$^7$ .................................................. C07C 27/00
(52) U.S. Cl. ....................... 518/700; 518/702; 518/703; 518/715; 518/721
(58) Field of Search .................................... 518/703, 702, 518/700, 721, 715

(56) References Cited

U.S. PATENT DOCUMENTS

| | | |
|---|---|---|
| 3,617,498 | 11/1971 | Kittrell . |
| 3,972,958 | 8/1976 | Garwood et al. . |
| 3,986,349 | 10/1976 | Egan . |
| 4,059,648 | 11/1977 | Derr et al. . |
| 4,092,825 | 6/1978 | Egan . |
| 4,197,184 | 4/1980 | Munro et al. . |
| 4,256,654 | 3/1981 | Schlinger et al. . |
| 4,404,088 | 9/1983 | Bachtel et al. . |
| 4,433,065 * | 2/1984 | Van Der Burgt et al. .......... 518/703 |
| 4,496,371 | 1/1985 | Urban et al. . |
| 4,501,655 | 2/1985 | Hilfman et al. . |
| 4,549,396 | 10/1985 | Garwood et al. . |
| 4,579,985 | 4/1986 | Minderhoud et al. . |
| 4,595,702 | 6/1986 | Chu et al. . |
| 4,605,639 | 8/1986 | Dyer et al. . |
| 4,617,288 | 10/1986 | Bell et al. . |
| 4,902,303 | 2/1990 | Den Bleyker . |
| 4,957,715 | 9/1990 | Grover et al. . |
| 4,992,081 | 2/1991 | Den Bleyker . |
| 4,994,428 | 2/1991 | Bell et al. . |
| 5,023,276 | 6/1991 | Yarrington et al. . |
| 5,026,472 | 6/1991 | Hoehn et al. . |
| 5,324,335 | 6/1994 | Benham et al. . |
| 5,324,336 | 6/1994 | Child . |
| 5,403,568 | 4/1995 | Stowe, Jr. . |
| 5,424,051 | 6/1995 | Nagji et al. . |
| 5,500,449 | 3/1996 | Benham et al. . |
| 5,504,118 | 4/1996 | Benham et al. . |
| 5,506,272 | 4/1996 | Benham et al. . |
| 5,543,437 | 8/1996 | Benham et al. . |
| 5,545,238 | 8/1996 | Brooker et al. . |
| 5,620,670 | 4/1997 | Benham et al. . |
| 5,621,155 | 4/1997 | Benham et al. . |
| 5,645,613 | 7/1997 | Benham et al. . |
| 5,666,800 * | 9/1997 | Sorensen et al. ................... 60/39.02 |
| 5,763,716 | 6/1998 | Benham et al. . |

OTHER PUBLICATIONS

Author: Marcel Dekker, Inc.; Title: The Fischer–Tropsch Synthesis in the Liquid Phase; Date: 1980; pp. 225–275.
Author: Chemical Engineering; Title: Technology to Cool Down Global Warming; Date: 1999; pp. 37,39,41.
Author: Alberto Rivalts; Title: Orimulsion. A new fuel for power generation and future feedstock use; Date: 1996; pp. 342–344.
Author: Charles B. Benham and Mark S. Bohn; Title: Maximization of Diesel Fuel Production from an Iron–Base Fischer–Tropsch Catalyst; Date: Dec. 1998; pp. 2–5.
Author: A.R. Jones; Title: The commericial combustion of Orimulsion; Date: 1997; pp. 318–339.
Author: Mark S. Bohn and Charles B. Benham; Title: A Comparative Study of Alternate Flowsheets Using Orimusion as Feedstock; Date: Jan. 1999; pp. 1–10.
Author: David Gray and Glen Tomlinson; Title: A Novel Configuration for Coproducing Fischer–Tropsch Fuels and Electric Power from Coal and Natural Gas; Date: Sep. 1997; pp. 1–6.
Author: Dr. Benham and Dennis Yakobson; Title: Optimization of Conversion of Low Hydrogen Containing Feedstocks ? Using Rentech's Gas–To–Liqiuds (GTL) Technology; Date: Jul. 1998; pp. 2–19.
Author: Schlesinge, Crowell, Leva, Storch; Title: Fischer-Tropsch Synthesis on Slurry Phase; Date: Jun. 1951; pp. 1474–1479.
Author: Arthur W. Tower III; Title: Gas–to–Liquids, Solids–yo–Liquids, Liquids–to–Liquids; Date: Dec. 18, 1998; Pages: whole book.

* cited by examiner

Primary Examiner—Shailendra Kumar
Assistant Examiner—J. Parsa
(74) Attorney, Agent, or Firm—Rick Martin; Patent Law Offices of Rick Martin P.C.

(57) ABSTRACT

Apparatus and processes for producing power, liquid hydrocarbons and carbon dioxide from heavy feedstocks, using a partial oxidation reactor to produce a synthesis gas, a Fischer-Tropsch reactor to convert the synthesis gas to hydrocarbon products and tail gases containing hydrogen and carbon dioxide, and a combined cycle plant to produce power from steam generated by recovering heat from the reactors and from combustible tail gases. By varying operating conditions and utilizing hydrogen for recycle to the Fischer-Tropsch reactor and/or hydrocracking wax products to produce lighter hydrocarbons, the process can selectively maximize the production of power, hydrocarbons or carbon dioxide. In preferred embodiments, the Fischer-Tropsch reactor can be a slurry reactor and can employ an iron-based catalyst.

13 Claims, 4 Drawing Sheets

PROCESSES FOR THE PRODUCTION OF HYDROCARBONS, POWER AND CARBON DIOXIDE FROM CARBON-CONTAINING MATERIALS

CROSS REFERENCED PATENTS

This application is a continuation-in-part of. U.S. application Ser. No. 09/212,374 filed Dec. 16, 1998 now abandoned.

FIELD OF INVENTION

This invention relates to improved processes for the conversion of carbon-containing liquid and solid feedstocks into valuable liquid hydrocarbon products by subjecting the feedstock to partial oxidation to produce synthesis gas and converting the synthesis gas into valuable products using a Fischer-Tropsch reactor and an iron-based catalyst. In these processes, high carbon feedstocks are converted to relatively low carbon fuels and the excess carbon dioxide is separated. The production of power, carbon dioxide or hydrocarbons can be selectively maximized to provide greater operational flexibility and economic return.

BACKGROUND OF THE INVENTION

Carbon dioxide emissions to the atmosphere have risen steadily since the beginning of the industrial revolution. At present, worldwide combustion of fossil fuels emits about 22 Gt of carbon dioxide to the atmosphere annually. The measured annual increase in atmospheric carbon dioxide is approximately 13 Gt. The difference between total output, which includes some additional emissions from deforestation and other anthropogenic sources, and the observed increase in atmospheric carbon dioxide is absorbed into natural sinks like the ocean and the biosphere. The substantial absorption indicates that the current state of the atmosphere is far from a steady-state equilibrium. The level of atmospheric carbon dioxide has risen by 30 percent from its pre-industrial value of 280 ppm to about 365 ppm today. Most of this rise (about 60 ppm) has occurred during the past 50 years.

The size of readily accessible fossil fuel deposits is extremely large. Easily accessible oil and gas may be limited, but oil shales, tar sands and coal deposits are virtually inexhaustable. Coal deposits alone are estimated at 10,000 Gt, which may be compared to a worldwide annual consumption of about 6 Gt of carbon. Methane hydrate deposits have become of interest recently, and may dwarf all other carbon resources. It can thus be concluded that fossil fuel resources are not ultimately limited by availability, or even for that matter by the cost of extraction. Past history suggests that technological advances can be expected to keep up with a gradual degradation of the quality of the energy resources. Furthermore, various hydrocarbon sources can be regarded as virtually interchangeable at some incremental cost over current energy costs.

Today, fossil energy contributes about 85 percent of the world energy supply. It is the cheapest, most readily available energy source. Thus, fossil energy is likely to remain the dominant energy resource for satisfying the growing world energy demand. World energy demand is growing rapidly as the developing countries are becoming industrialized. The potential for further growth is extremely large. A world population of 10 billion with a per capita energy consumption equal to that of the U.S. today would consume ten times more energy than the world consumes today. Even though most energy forecasts assume far less growth over the next fifty years, higher growth resulting in additional improvements in living standards and a consequent increase in political stability would be highly desirable. These lower estimates actually assume that economic growth in the first half of the 21st century will be smaller than that in the second half of the 20th century. Even so, growth in energy demand will still be very large. Even with the extensive use of alternative forms of energy, the demand for fossil fuels will increase significantly.

Unless environmental considerations artificially limit the use of fossil energy, there is no end in sight for the demand for fossil fuels. Combustion of such quantities of fossil fuels could drive atmospheric carbon dioxide levels very much higher. The available 10,000 Gt of carbon correspond to 4700 ppm of atmospheric carbon dioxide. While the detailed effects of carbon dioxide on climate and environment are still debated, it is known that carbon dioxide is a greenhouse gas which can cause climate change. Carbon dioxide affects the acidity of the ocean, it is of physiological importance and thus can directly affect the ecological balance of species. To continue current energy consumption patterns could eventually lead to a doubling of natural carbon dioxide levels. To stabilize carbon dioxide at 600 ppm would require a drastic reduction in carbon dioxide emissions, ultimately to about 30 percent of those of 1990. For 10 billion people sharing in such a carbon dioxide budget, the per capita allowance would come to about 3 percent of that of the average U.S. citizen today.

In summary, it appears to be extremely difficult to stop the growth of fossil energy demand, yet to stabilize atmospheric carbon dioxide levels would require a drastic reduction in carbon dioxide emissions. The logical solution appears to be methods of collecting and subsequently disposing of the gas after it has been generated. While it is acknowledged that it is easier to collect carbon dioxide from a concentrated stream than from a dilute stream, it has actually been suggested that carbon dioxide could be collected from the atmosphere to accomplish these objectives. See Lackner et al., "Carbon Dioxide Extraction From Air: Is it an Option?", Proceedings of 24th International Technical Conference on Coal Utilization and Fuel Systems, March 1999, Clearwater, Fla.

Given the expected increases of carbon dioxide in the atmosphere, it is clearly desirable to separate this gas from emissions by power plants or other sources, or even from the atmosphere itself, in order to dispose of or sequester carbon dioxide. Sequestration of carbon dioxide means its removal or segration from the atmosphere for a significant period of time, if not permanently. There are various approaches, including disposal in the deep ocean, injection into underground reservoirs and chemical stabilization as carbonate minerals. It is becoming increasingly important to prevent emissions from systems involving the combustion of fossil fuels from increasing the proportion of carbon dioxide in the air. Such removal and disposal, whether viewed as permanent sequestration or longterm term segregation, has economic value which can be awarded by national authorities as tax or pollution credits. For example, Norway presently levies a tax of over $50 U.S. per ton on carbon dioxide emissions. (See "Technology to Cool Down Global Warming," infra.) Equivalent amounts may be awarded to organizations sequestering carbon dioxide from combustion processes.

A significant fraction of the crude oil fed to a refinery consists of heavy material generally having a high content of sulfur. This material is oftentimes an environmental liability to the refinery with high disposal costs. Recently it has been considered that a more economical solution to the problem is to convert the heavy crude oil to synthesis gas using partial oxidation (POX).

The partial oxidation (POX) reaction can be expressed as:

$$CH_z + 0.5O_2 \rightarrow z/2 H_2 + CO$$

where z is the H:C ratio of the hydrocarbon feedstock. The water gas shift (WGS) reaction also takes place:

$$H_2O + CO \leftrightarrow H_2 + CO_2$$

The synthesis gas can then be used as fuel in a gas turbine to generate electrical power. An example of this approach is the api Energia S.p.A integrated combined cycle plant (IGCC) described in the Dec. 9, 1996 issue of the Oil & Gas Journal. In many instances, it is not desirable or practical to use all of the synthesis gas produced in the POX reactor for production of electricity. In these instances it may be desirable to convert some or all of the synthesis gas to liquid hydrocarbons which are free of aromatics and sulfur using Fischer-Tropsch (FT) chemistry.

The Fischer-Tropsch (FT) synthesis reaction is expressed by the following stoichiometric relation:

$$2n\, H_2 + nCO \rightarrow C_nH_{2n} + nH_2O$$

The aliphatic hydrocarbons produced by the Fischer-Tropsch reaction have an H:C atom ratio of 2.0 or greater.

Fischer-Tropsch catalysts such as iron-based composites also catalyze the water gas shift (WGS) reaction:

$$H_2O + CO \leftrightarrow H_2 + CO_2$$

If all of the water produced in the FT reaction were reacted with CO in the WGS reaction, then the overall consumption of hydrogen would be one-half of the consumption of carbon monoxide. If none of the water were reacted in the WGS reaction (no WGS activity) then the consumption of hydrogen would be twice the consumption of carbon monoxide.

The oil produced in the FT reaction can be blended and processed with the lighter refinery crude oil, thereby lowering the average aromatic and sulfur content of distillate fuels.

Due to the relatively low hydrogen content of the heavy crude oil, any FT catalyst useful in converting synthesis gas produced by partial oxidation of heavy crude oil must possess some water gas shift activity. Therefore, modern cobalt-based FT catalysts which have very little WGS activity cannot generally be used when the POX feedstock is a heavy crude oil, coke or coal. However, iron-based catalysts as described in U.S. Pat. No. 5,504,118 have high WGS activity and are preferred for use with low-hydrogen feedstocks.

For a natural gas feedstock which has a high H:C ratio, U.S. Pat. Nos. 5,620,670 and 5,621,155 teach that carbon dioxide recycle back to the synthesis gas producing step (either POX or steam reforming) decreases the excessively high $H_2$:CO ratio of the synthesis gas and increases the yield of Fischer-Tropsch (FT) hydrocarbons and the attendant carbon conversion efficiency.

In the case of low H:C ratio feeds, steam reforming is not a viable means for producing synthesis gas due to the inevitable formation of carbon when using these high carbon feedstocks. Carbon deposition on a reforming catalyst cannot be tolerated. Also, solid fuels are unsuitable for steam reforming. Thus, the only viable option for gasifying high C:H feeds is POX.

In the instant case, the aforementioned carbon dioxide recycle back to a POX reactor is not useful due to the lack of sufficient hydrogen.

Another means for increasing the hydrocarbon yield and carbon conversion efficiency of a system is to recycle part of the tail gas to the inlet of the POX unit. However, the amount of tail gas recycle is limited by the resulting low $H_2$:CO ratio in the synthesis gas produced in the POX caused by the large amount of $CO_2$ in the tail gas.

The use of combined partial oxidation and Fischer-Tropsch reactors permits the conversion of a variety of high-carbon solid and liquid fuels to liquid hydrocarbons and other products which have lower C:H atom ratios and can thus be combusted or otherwise used with net lower emissions of carbon dioxide to the atmosphere. In the present invention, carbon dioxide can be efficiently removed from tail gases in the process and sequestered to reduce the net carbon dioxide emissions. Due to environmental and political considerations, there is increasing interest in reducing carbon dioxide emissions associated with combustion energy, and in trapping and sequestering such gases as are emitted. See "Technology to Cool Down Global Warming," Chemical Engineering, January 1999 (pp. 37–41). Because of these inherent advantages, Fischer-Tropsch technology is attracting increasing attention as a means for utilizing resources such as coal in efficient and environmentally friendly ways. Countries such as China and India, having large coal reserves and needs for liquid hydrocarbon fuels, could benefit immensely from such processes. See, e.g. Arthur W. Tower III, "Fischer-Tropsch Technology," published by Howard, Weil, Labouisse, Friedrichs of New Orleans, La., Dec. 18, 1998. See also "State of the Art in GTL Technology," presented by Dr. Joe Verghese of ABB Lummus Global at the Gas to Liquids World Forum, London, November 1998.

Information about Orimulsion®, an aqueous emulsion of bitumen produced in Venezuela, can be found in various publications, including A. R. Jones' "The Commercial Combustion of Orimulsion," in the book *Combustion & Emissions Control III*, ed. M. Adams, Institute of Energy, London 1997 (pp. 318–339). See also Franzo Marruffo et al., "Orimulsion an alternative source of energy," presented at the 22nd International Technology Conference Coal Utility Fuel Systems at Clearwater, Fla., March 1997 (Coal & Slurry Technology Ass'n), pp. 13–24. Also pertinent is Rivalta et al., "Orimulsion™—A New Fuel for Power Generation and Future Feedstock Use," Polymer News, Vol. 21, No. 10 (pp. 342–344).

U.S. Pat. No. 4,549,396 (Mobil Oil) discloses a process of converting coal to synthesis gas by partial oxidation with air, then converting the synthesis gas to liquid and gaseous hydrocarbons. The gas and liquid products are both used in a gas turbine to generate electrical power.

U.S. Pat. No. 4,433,065 (Shell Oil) discloses a process for converting pulverized coal to a synthesis gas, which is catalytically converted to a gas containing hydrocarbons. Part of the product gases are recycled to the gasification stage.

U.S. Pat. No. 4,092,825 (Chevron Research) discloses a process of gasifying solid carbonaceous feedstocks to form a synthesis gas, a portion of which is contacted with a Fischer-Tropsch catalyst to form condensable hydrocarbons. A second portion of the synthesis gas can be combusted to generate electrical power, while the condensable hydrocarbons are used as fuel to generate more power to meet peak loads. This patent is a C.I.P. of U.S. Pat. No. 3,986,349.

U.S. Pat. No. 3,972,958 (Mobil Oil) discloses an integrated process for converting coal to high octane gasoline by gasifying the coal to form a synthesis gas containing methane, then contacting the gas with at least one catalyst to form products including gasoline and light hydrocarbons.

Gray and Tomlinson of Mitretek Systems disclose in "$CO_2$ Emissions from Fischer-Tropsch Fuels," presented at Fuels, Lubricants, Engines and Emissions meeting (sponsored by EFI and DOE) at Tucson, Ariz. on Jan. 18–20, 1999 a "coproduction cofeed" concept. Coal-derived synthesis gas is reacted in a liquid synthesis reactor to form liquid hydrocarbons, and unreacted synthesis gas is combined with natural (gas for combustion in a downstream combined cycle power generation unit.

U.S. Pat. No. 5,324,335 (Applicants) discloses the use of Fischer-Tropsch liquids as a diesel fuel additive.

U.S. Pat. No. 5,500,449 (Applicants) discloses a method of recovering a heavy Fischer-Tropsch wax and thermally cracking the wax to produce diesel and naphtha fractions.

U.S. Pat. No. 5,504,118 (Applicants) discloses methods for manufacturing and activating iron-based Fischer-Tropsch catalysts.

U.S. Pat. No. 5,506,272 (Applicants) discloses Fischer-Tropsch diesel fuel products.

U.S. Pat. No. 5,543,437 (Applicants) discloses methods for producing Fischer-Tropsch products from coal-derived synthesis gas. The products are produced at varying rates due to varying amounts of the synthesis gas being fed to a power generation facility.

U.S. Pat. No. 5,620,670 (Applicants) discloses a process of producing synthesis gas in a steam reformer, reacting the synthesis gas in a Fischer-Tropsch reactor, then separating carbon dioxide and recycling same to the reformer to enhance carbon conversion efficiency and product yield.

U.S. Pat. No. 5,621,155 (Applicants) discloses methods of producing synthesis gas which is reacted in a Fischer-Tropsch reactor, then separating and recycling carbon dioxide to the steam reformer or partial oxidation reactor or recycling light hydrocarbons from the Fischer-Tropsch reactor to the reactor inlet, all to increase carbon conversion efficiency.

U.S. Pat. No. 5,645,613 (Applicants) discloses the use of Fischer-Tropsch liquids as a blending stock for diesel fuel to produce oxygenated diesel fuels.

Even though the technology for conversion of high-carbon feedstocks to synthesis gas and the subsequent production of Fischer-Tropsch liquids is well developed, the growing demand for energy coupled with the need to limit emissions of "greenhouse gases" and/or to sequester carbon dioxide which is emitted by combustion processes create a need for more efficient and flexible processes which can meet the demand for power and hydrocarbon production while separating carbon dioxide for sequestration or disposal.

SUMMARY OF THE INVENTION

It is an aspect of this invention to provide a Fischer-Tropsch process using an iron-based catalyst where the hydrocarbon-containing feedstock to the first stage gasifier has a much lower H:C ratio than natural gas which generally has a H:C ratio in the range of 3.0 to 4.0.

It is a further aspect of this invention to increase the hydrocarbon yields from a POX/FT system. Alternatively, it is an aspect of this invention to increase the production of power from a combined cycle system associated with the system of the invention, and/or to increase the amount of carbon dioxide separated from the FT reactor tail gases in order to sequester this gas from the atmosphere.

It is another aspect of this invention to produce a synthesis gas from carbon-bearing feedstocks having an H:C atom ratio of less than about 2.0 which can be used for combustion in boilers for the production of steam in an electric power generation system and when the demand for the electric production decreases, the synthesis gas can be used for a process for producing hydrocarbons having an average H:C atom ratio of 2.0 or greater.

The process produces hydrocarbons having an average H:C atom ratio of 2.0 or greater from carbon-bearing feedstocks having an H:C atom ratio of less than 2.0. The carbon-bearing feedstock is reacted with an oxidizing gas such as oxygen or air containing oxygen and steam in a partial oxidation reactor to produce a mixture of gases containing hydrogen and carbon monoxide having a molar ratio of $H_2$:CO of greater than 0.6. Then the mixture of gases containing hydrogen and carbon monoxide is reacted in a Fischer-Tropsch synthesis reactor containing a catalyst which catalyzes both hydrocarbon-forming reactions and the water gas shift reaction. The product hydrocarbons are condensed out from the unreacted hydrogen, carbon monoxide and other gases referred to as tail gases.

The present invention allows the production of FT liquid hydrocarbons, electrical power and carbon dioxide, all from high-carbon feedstocks. The claimed apparatus and processes allow at least one of these outputs to be selectively maximized according to economic requirements. The process is aimed at future requirements when carbon dioxide sequestration may be required and there will be economic benefits to doing so. Under such conditions, the sacrifice of outputs of high value FT liquids and/or electrical power to preferentially produce carbon dioxide will be a necessary capability.

Enabling features of the invention include the following:

Iron catalyst: Iron-based catalysts allow the production of FT liquids from synthesis gases with low $H_2$:CO ratios, such as obtained from high-carbon feedstocks. Also, iron catalysts are active towards the water-gas shift reaction, which produces carbon dioxide in the reactor product stream. Reducing the net carbon dioxide produced from high-carbon feedstocks is an increasingly important capability.

High-pressure $CO_2$: Carbon dioxide is produced in the FT product stream at high pressure and at high concentration. Under these conditions, it is much more economical to separate the $CO_2$ from the FT process tail gas, compared, e.g. to the removal of dilute, low pressure $CO_2$ from a power plant stack gas. (Typical $CO_2$ concentration in stack gas from coal-fired power plants is around 15 percent, while the equivalent concentration for natural gas-fired plants is less than 10 percent, according to Plasynski et al., "Carbon Mitigation: A Holistic Approach to the Issue," Proceedings of 24th International Technical Conference on Coal Utilization & Fuel Systems.) This results from the fact that the FT reactor operates more efficiently at high pressure. The unique combination of a high-pressure FT reactor and an iron-based catalyst makes it easier to sequester $CO_2$ from the high-carbon feedstocks without the need for additional unit operations such as a separate shift reactor.

Hydrogen recycle: Hydrogen recycle from the FT product stream to the FT feed can optionally increase the $H_2$:CO ratio of the synthesis gas fed to the FT reactor. This is beneficial, because although iron catalysts can handle low $H_2$:CO ratio synthesis gas, higher $H_2$:CO ratios produce less $CO_2$ and greater yields of FT liquids. In addition, unless there is a local high-value market for hydrogen, it would be used to produce power. If power is higher valued then the hydrogen, less hydrogen would be recycled and more would be used to produce power. If a mixed FT product stream is acceptable, hydrogen would not be needed for hydrocracking, and it may be possible to eliminate the hydrogen removal step.

Process adjustability: The process can be operated to optimize the relative production rates of FT liquids, power and $CO_2$. The FT reactor can be designed and operated (as to size and temperature, pressure and space velocity) to produce more or less FT liquids, and synthesis gas can be bypassed around the FT reactor directly to the combined cycle plant to produce more power or for load leveling. The production of carbon dioxide can be traded off against hydrocarbon production by altering catalyst operating variables such as temperature and space velocity. Additionally, the input of water to the FT reactor can be increased directly or by extracting less heat from the synthesis gas via the heat exchanger to increase $CO_2$ production in the FT reactor.

Combined cycle plant: A combined cycle plant associated with the process generates power from both a combustion turbine and a steam turbine. This is well suited to a process including a FT reactor, since both combustible tail gases and steam are produced. Combustible tail gas is produced by the FT reactor as light overhead gases. Steam is produced by cooling the gasifier, effluent from the FT reactor and by heat recovery from the gas turbine exhaust.

Co-feeding natural gas: Feeding natural gas to the gasifier in addition to the high-carbon feedstock allows one to supply the necessary hydrogen to the gasifier with less water. This reduces the energy penalty of vaporizing water and significantly increases plant efficiency. Alternatively or in addition to this use of natural gas, natural gas can optionally be fed directly to the combustion turbine when increase power production is desired.

In accordance with the invention, a process for producing power, carbon dioxide and hydrocarbons having an average H:C atom ratio of 2 or greater from carbon-bearing feedstocks having an H:C atom ratio of less than 2 is provided which permits the selective maximization of at least one of the products power, hydrocarbons and carbon dioxide, and comprising steps of:

a) reacting a carbon-bearing feedstock with an oxidizing gas and steam in a partial oxidation reactor to produce a mixture of gases containing hydrogen, carbon monoxide and carbon dioxide having a molar ratio of $H_2$:CO of greater than about 0.6;

b) reacting the mixture of gases containing hydrogen and carbon monoxide in a Fischer-Tropsch synthesis reactor containing a catalyst which catalyzes both hydrocarbon-forming reactions and the water gas shift reaction;

c) condensing the product hydrocarbons from unreacted hydrogen, carbon monoxide and other gases (tail gases);

d) separating the product hydrocarbons into naphtha, diesel and wax fractions;

e) removing at least a portion of carbon dioxide from the tail gases; and f) producing steam from heat recovered from at least the partial oxidation reactor and the Fischer-Tropsch reactor, directing the steam to the steam turbine of a combined cycle plant, and directing at least the tail gases to the gas turbine of the combined cycle plant to produce power.

Optionally, hydrogen can be separated from the tail gases and utilized for recycle to the partial oxidation reactor and/or hydrocracking wax F-T products to form more liquid hydrocarbon products. Natural gas can be introduced into the partial oxidation reactor to supplement the feedstock. Natural gas can also be fed to the gas turbine of the combined cycle plant to increase power production. The production of carbon dioxide in the F-T reactor can be increased relative to hydrocarbon production by increasing the water content of the synthesis gas fed to the F-T reactor, preferably by decreasing the amount of heat extracted from the partial oxidation reactor effluent.

Further in accordance with the invention, apparatus for carrying out the process is provided, comprising the following operationally-connected components:

a) a partial oxidation reactor;

b) means for removing acid gases (such as $H_2S$ and COS) from the synthesis gas leaving the partial oxidation reactor;

c) a Fischer-Tropsch reactor connected to receive the synthesis gas;

d) heat exchangers connected to remove heat from the partial oxidation reactor, Fischer-Tropsch reactor and other heat sources and generate steam;

e) means for separating carbon dioxide and/or hydrogen from the F-T tail gases;

f) means for removing hydrocarbon products from the Fischer-Tropsch reactor effluent and separating them into fractions;

g) optionally, a hydrocracking reactor for utilizing hydrogen separated by (e) to hydrocrack wax fractions of the Fischer-Tropsch hydrocarbon products to form more liquid products; and h) a combined cycle plant including gas and steam turbines for production of power from the steam and tail gases recovered from the partial oxidation reactor—Fischer-Tropsch reactor complex.

Other aspects of this invention will appear from the following description and appended claims, reference being made to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENTS

Candidate feedstocks for the processes of the invention include those having a low percentage of hydrogen compared to carbon on an atom basis. Candidate feedstocks include refinery residual oil (low API gravity fuel oil, VacResid, H-oil Bottoms, 0 degrees API Asphalt, etc.), petroleum coke, coal, tires, biomass, and mixtures of these feedstocks. Other suitable feedstocks include aqueous emulsions of bitumen such as Orimulsion®, available commercially from Venezuelan sources. (Bitumen is a generic term describing mixtures of hydrocarbons derived from natural and/or pyrogenic origins.)

Refinery oil residues are relatively high in carbon because they contain a high percentage of ring compounds including aromatics. The average H:C atomic ratios of various candidate feedstocks are:

| Feedstock | H:C Atom Ratio |
|---|---|
| Refinery Feedstocks: | |
| 9.6 API Fuel Oil | 1.35 |
| 4.3 API VacResid | 1.37 |
| H-Oil Bottoms | 1.26 |
| 0 deg. API Asphalt | 1.26 |
| Delayed Petroleum Coke | 0.53 |
| Fluid petroleum Coke | 0.28 |
| Coals: | |
| Pittsburgh #8 | 0.83 |
| French | 0.80 |
| Utah | 0.84 |
| German | 0.75 |
| S. African | 0 64 |
| Biomass: | |
| Wood Wastes | 1.49 |
| Wheat Straw | 1 50 |
| Tires: | 1.25 |
| Orimulsion ®: | 2.12 |

The oxidizing gas which is used can be oxygen in a relatively pure form such as at a purity of greater than about 90 percent by volume or it can be in the form of air where the air contains greater than about 20 percent oxygen by volume.

Any suitable source of natural gas or the equivalent can be used to provide supplementary feed to the partial oxidation reactor and/or fuel to the gas turbine of the combined cycle plant. It would of course be convenient if the system of the invention were located adjacent to a direct source of natural gas. It is also advantageous to locate the system in a refinery, where various feedstocks are available and hydrocarbon products and power can be readily used.

Any suitable partial oxidation reactor capable of handling heavy feedstocks can be employed, e.g. the type(s) disclosed in Texaco's U.S. Pat. Nos. 4,992,081; 4,902,303 and 51545, 238, all of which are incorporated herein by reference, and in additional patents listed in column 1 of U.S. Pat. No. 5,545,238.

Typical heat exchangers useful in refinery and power plant applications can be used to recover waste heat from suitable sources within the system and generate steam for use in the combined cycle plant.

Suitable apparatus for removing acid gases such as $H_2S$ and COS from the synthesis gas produced by the partial oxidation reactor can be used. Suitable apparatus includes wet or dry scrubbing systems: an example is disclosed in U.S. Pat. No. 5,403,568, which is incorporated herein by reference.

Any suitable Fischer-Tropsch reactor capable of converting synthesis gases produced from heavy feedstocks to typical Fischer-Tropsch hydrocarbon products can be used. Typical reactors are disclosed in Rentech's U.S. Pat. Nos. 5,506,272; 5,543,437 and 5,763,716, which are incorporated herein by reference. Preferably, the Fischer-Tropsch reactor is a slurry reactor, such as disclosed in the above Rentech patents and described in the article entitled "Fischer-Tropsch Synthesis in Slurry Phase" by Schlesinger et al. in *Engineering and Process Development*, Vol. 43, No. 6 (June, 1951), pp. 1474–1479, and by Kolbel and Ralek in "The Fischer-Tropsch Synthesis in the Liquid Phase," *Catalyst Review-Science Engineering*, Vol. 21(2), pp. 225–274 (1980).

Slurry reactors are vertical vessels in which fine powdered catalyst is suspended in molten wax. The synthesis gas is introduced into the bottom of the reactor and F-T products emerge from the top and side of the reactor. The heavy F-T products are filtered from the wax/catalyst slurry.

The Fischer-Tropsch catalyst should be a catalyst which simultaneously catalyzes the production of hydrocarbon products from a synthesis gas and activates the water gas shift reaction. The catalyst is preferably an iron-based catalyst such as disclosed in U.S. Pat. No. 5,504,118, which is incorporated herein by reference. As stated in column 4 of the patent, the composition, preparation and activation of the catalyst are all important to its operation. The preferred catalyst is an unsupported precipitated iron catalyst promoted with copper and potassium, which is prepared using elemental iron and copper as starting materials. The catalyst can be prepared as disclosed in column 11 of the patent, and activated as disclosed in columns 12.

The $H_2$ separation devices based on membranes are commercially available from Monsanto, W. R. Grace & Co., and Dow Corning. Another technology for $H_2$ separation from a mixed gas stream uses pressure swing absorption (PSA). Suitable apparatus for separating carbon dioxide from tail gases include various absorption systems disclosed in U.S. Pat. Nos. 4,496,371; 4,957,715 and 5,424,051, which are incorporated herein by reference. Removal of carbon dioxide from the relatively high pressure gases emerging from the Fischer-Tropsch reactor at pressures in the range of from about 100 to about 500 psig, and temperatures in the range of from about 100° to about 300° F. is advantageous when compared with the alternative of removing the gas from atmospheric pressure stack gases from furnaces or other combustion systems, which typically contain less than 15 percent carbon dioxide. In the processes of the invention, the F-T reactor effluent can contain in the range of from about 15 to about 60 volume percent carbon dioxide, preferably from about 20 to about 55 and most preferably from about 25 to about 50 volume percent.

The product separation means will generally consist of partial condensers, distillation columns, and possibly hydrocracking units, all well known to those possessing ordinary skill in the art. Tail gas which is not recycled can be used for fuel in the process, including the gas turbine of the combined cycle plant.

Optionally, a typical hydrocracking reactor is provided to utilize hydrogen separated from tail gases to crack wax products of the Fischer-Tropsch reactor into liquid hydrocarbons. Suitable hydrocracking reactors and catalysts are disclosed in U.S. Pat. Nos. 3,617,498; 4,197,184; 4,404,088; 4,501,655 and 5,026,472, which are incorporated herein by reference.

A suitable combined cycle plant is provided which includes at least one steam turbine to which steam recovered from the process can be fed, and a gas turbine to burn fuels which can include natural gas, tail gases from the Fischer-Tropsch reactor, hydrogen and naphthas separated from the hydrocarbon products. Such combined cycle plants are well known in the art.

Figure 1:
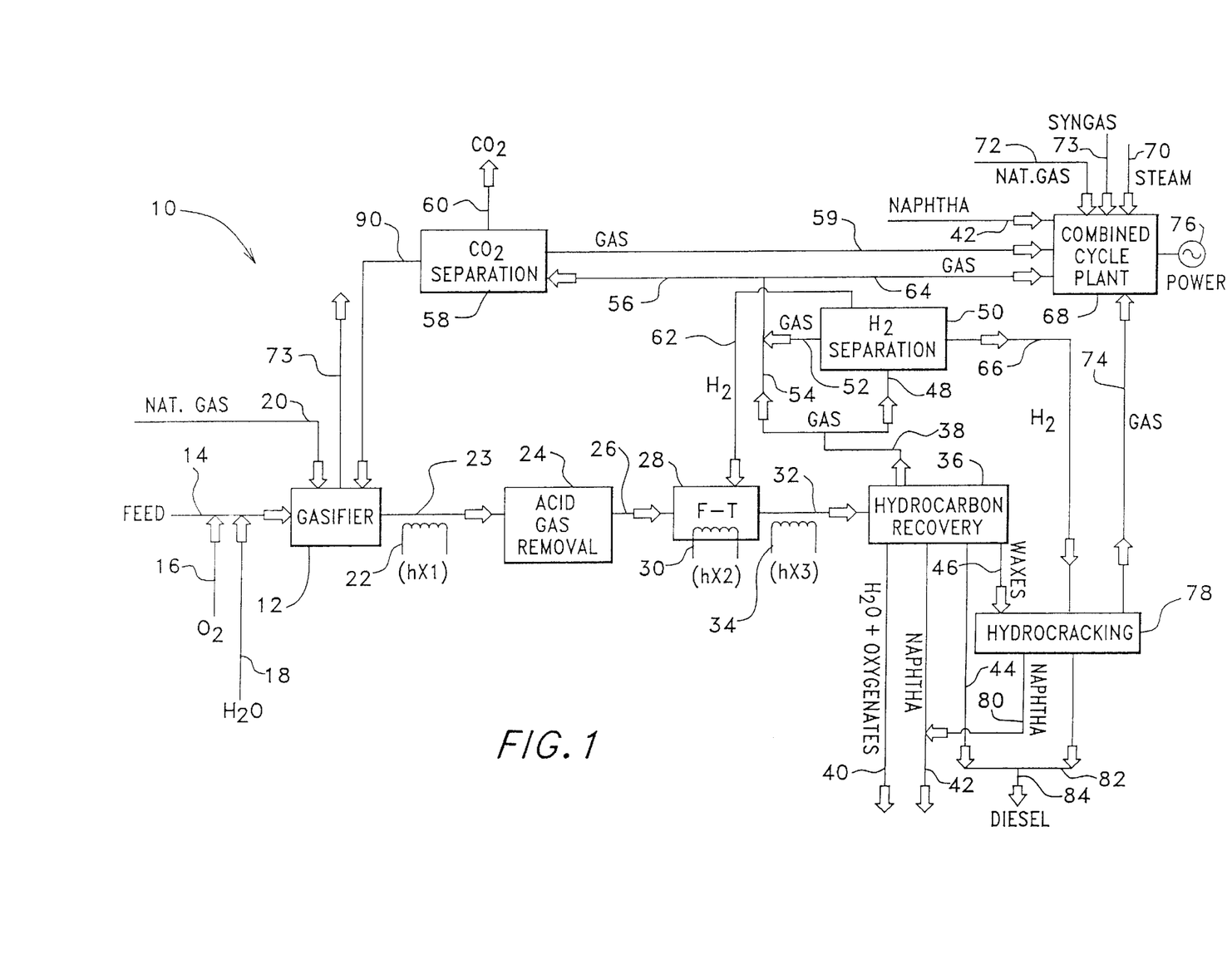
FIG. 1 is a flow sheet comprehensively illustrating the processes and apparatus of the invention in their most general forms.

Turning now to the drawing, FIG. 1 illustrates the system 10 of the invention and the processes carried out therein. Partial oxidation reactor 12 is provided with feed 14 as described above, plus oxygen 16 and water 18. Optionally, natural gas 20 can be introduced to supplement the feed.

The synthesis gas produced by the partial oxidation reactor 12 is passed to a Fischer-Tropsch reactor 28 via connectors 23 and 26. Preferably apparatus 24 for removing acid gases such as $H_2S$ and COS is included between the partial oxidation reactor 12 and Fischer-Tropsch reactor 28. Heat exchangers 22, 30 and 34 are provided to remove heat from the partial oxidation reactor, Fischer-Tropsch reactor and FT effluent connector 32, respectively. Additional heat exchangers (not shown) can be placed wherever the system offers a significant source of heat. All the heat exchangers are also steam generators, producing steam to drive the steam turbine(s) (not shown) of the combined cycle plant 68 via 70.

Hydrocarbon recovery unit 36 separates hydrocarbon products from F-T tail gases delivered through connector 32 and divides the products into fractions containing water and oxygenates 40, naphtha 42, diesel 44 and waxes 46. Optionally, hydrocracking reactor 78 is provided to crack wax products 46 into further naphtha and diesel fractions 80 and 82, respectively. Tail gases 74 generated in the hydrocracking reactor are typically burned in the gas turbine (not shown) of the combined cycle plant 68.

Tail gases 38 discharged from the hydrocarbon recovery unit 36 pass through optional hydrogen separation unit 50 and through carbon dioxide separation unit 58. Separated hydrogen is used by recycling to the Fischer-Tropsch reactor via connector 62 to increase the $H_2:CO$ ratio in the synthesis gas entering the F-T reactor and/or directed via connector 66 for hydrocracking wax products in hydrocracking reactor 78. A portion of tail gases 64 can pass directly to the combined cycle plant 68 for combustion in the gas turbine (not shown).

(Similarly, tail gases remaining after separation of carbon dioxide and hydrogen (59 and 52, respectively) also are directed to the gas turbine. Such tail gases can also be recycled to gasifier 12 via 90.

Separation of carbon dioxide from the F-T effluent is advantageous because it can be sequestered for environmental purposes. For example, the carbon dioxide recovered can be transported and injected into the depths of the sea, used for enhanced oil recovery from underground formations or employed in the synthesis of materials such as urea. A plant for producing such products (not shown) can be installed adjacent to the system of the invention.

Combined cycle plant 68 is configured and connected to permit the employment of all available steam and combustible gases, and can be operated to maximize the production of power when and where this is more valuable than the Fischer-Tropsch products. The principal feed for the gas turbine of this plant is tail gases 32 from the Fischer-Tropsch reactor (which may have been processed by further gas separators or the hydrocracking reactor). This fuel can be augmented by feeding natural gas 72 and/or naphtha fractions 42 of the F-T products to increase power production. The steam and gas turbines are connected to electrical generators to produce electrical power. To maximize power without production of F-T products, all the synthesis gas 73 from the POX can be sent to the gas turbine of combined cycle plant 68, thus bypassing F-T reactor 28.

EXAMPLES

Having described the basic aspects of the invention, the following examples are given to illustrate specific embodiments thereof.

Examples were calculated using a proprietary computer program for thermodynamic calculations based on apparatus for configurations and process conditions designed to maximize the production of power, carbon dioxide and hydrocarbons, respectively. The functions performed by the computer program included modeling the POX reactor, the FT reactor, all recycle loops, the separation processes and power generation.

Figure 2:
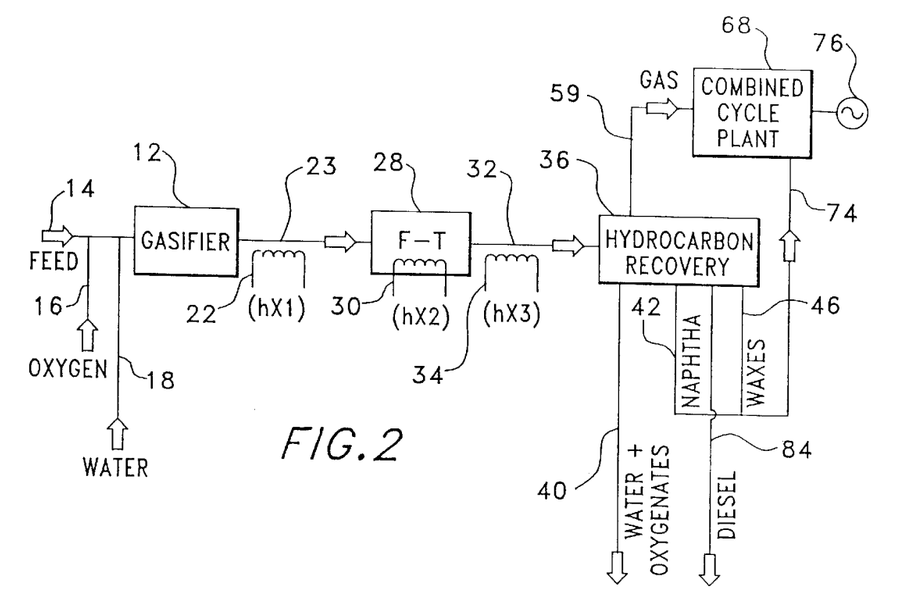
FIG. 2 is a flow sheet illustrating the process and apparatus of the invention configured for maximum power production.
Figure 3:
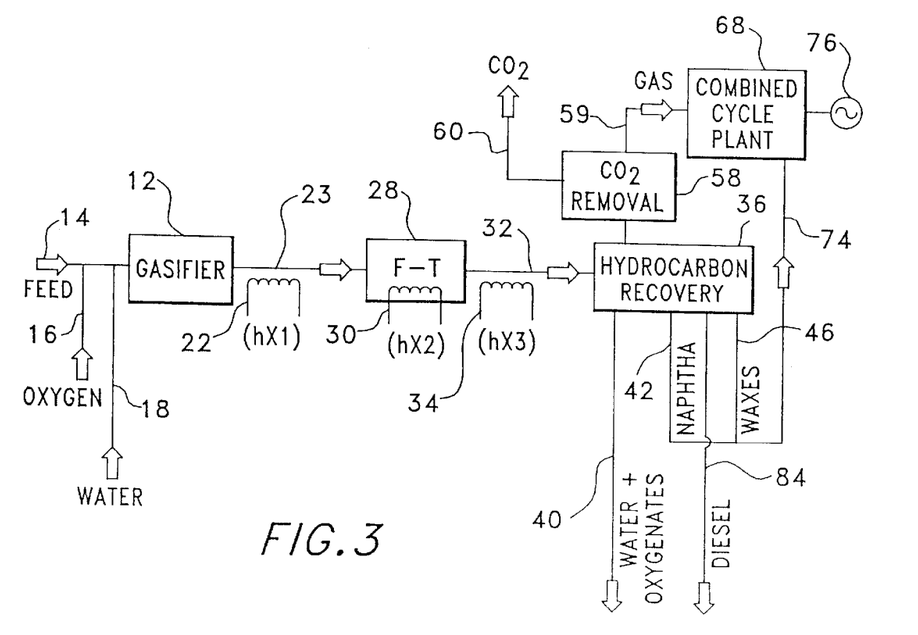
FIG. 3 is a flow sheet illustrating the process and apparatus of the invention configured for maximum carbon dioxide production.
Figure 4:
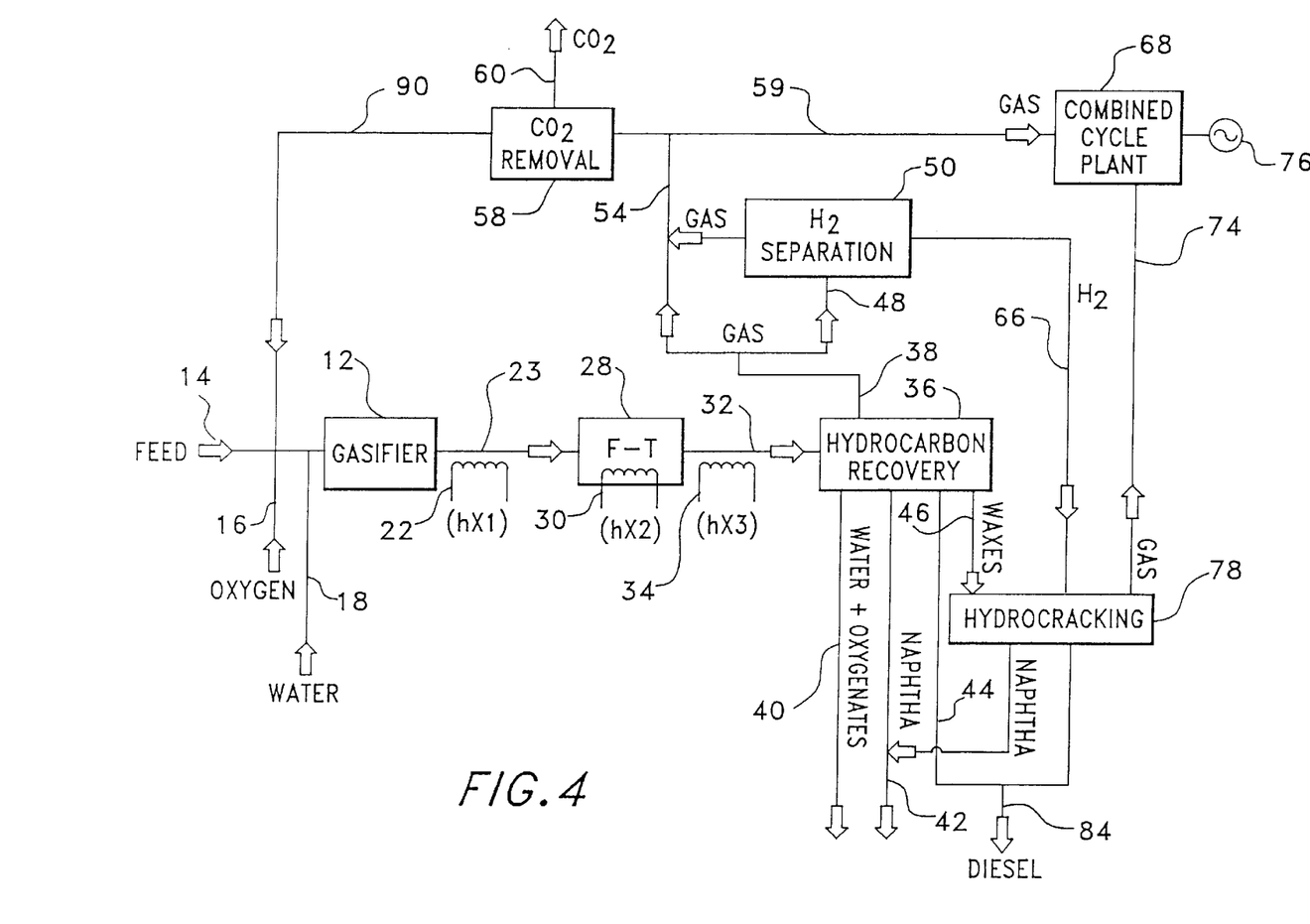
FIG. 4 is a flow sheet illustrating the process and apparatus of the invention configured for maximum hydrocarbon production.

The examples are based upon the flow sheets of FIGS. 2, 3 and 4. All three flow sheets assume a feedstock feed rate of 2500 tons per day. The feedstock (Orimulsion) contains 60.7 weight percent carbon, 7.6 weight percent hydrogen, 0.4 weight percent nitrogen, 2.6 weight percent sulfur, 0.1 weight percent ash and 28.6 weight percent moisture. An efficiency of power generation from the steam turbine is 33 percent and of the combined cycle plant is 55 percent, based upon the lower heating value of the fuel.

Examples 1, 1A

Maximum Power Flow Sheet

In this flow sheet (FIG. 2) the F-T plant converts syngas from the gasifier into liquid hydrocarbons. Tail gas from the F-T plant is burned in the combined cycle plant to produce electricity. Steam from the three heat exchangers (22, 30, 34) is sent to the steam turbine part of the combined cycle plant 68 to produce electricity. Power production is maximized by burning the F-T naphtha and wax fractions in the combined cycle because these hydrocarbon products are generally of less value than the diesel fraction. This gives a power production of 271 MWe and a diesel production of 869 bbl/day. If the syngas from the gasifier is sent directly to the combined cycle, i.e., no hydrocarbons are produced via F-T reactions (Example 1A), the power production is 330 MWe. It could be argued that the latter configuration produces the maximum power, but in the absence of F-T hycrocarbon production.

Examples 2 and 2A

Maximum $CO_2$ Flow Sheet

By removing all $CO_2$ from the F-T tail gas prior to the combined cycle as shown in FIG. 3, one can easily capture a large flow of $CO_2$, approximately 46 MMSCFD. Power production will be approximately the same as in the maximum power flow sheet of Example 1, 271 MWe, and diesel production is also the same, 869 bbl/day. This example illustrates that if the value of the $CO_2$, e.g. through environmental credits, is sufficiently high, the extra capital cost of the $CO_2$ removal system can be justified and there will be no penalty in power production or F-T liquid production. This example (2) illustrates the ease with which $CO_2$ can be removed from the tail gas of an iron catalyst-based F-T reactor. The amount of $CO_2$ removed can be varied by adjusting the size of the $CO_2$ removal system to maximize plant revenues.

The production of $CO_2$ by the F-T reactor system can be further increased by taking advantage of the water-gas shift activity of the iron F-T catalyst preferably used in the processes of the invention. The equilibrium of the water-gas shift reaction (shown above on page 7) can be shifted to the right by forcing more water vapor into the F-T reactor. The results will be increased production of $CO_2$, which can then be separated from the F-T effluent. Water can be introduced directly, but preferably the same effect is achieved by reducing the cooling effect of heat exchanger 22. Since the effluent from the gasifier is cooled less, the partial pressure of water vapor entering the F-T reactor will be greater, with the predictable effects on the water-gas shift reaction equilibrium. The resultant yield of hydrocarbons will be less, but under certain economic conditions, the increased production and separation of $CO_2$ will make up for this.

The computer simulation program is used to determine and compare the yields of $CO_2$ and hydrocarbons for the cases of Example 2 and the same simulation (Example 2A) in which more water is allowed to enter the F-T reactor. The results are shown in Table 1 below.

TABLE 1

| Example | case | water to FT vol % | $CO_2$ yield MMSCFD | diesel yield bbl/day | power MWe |
|---|---|---|---|---|---|
| 2 | Baseline max $CO_2$ | 0 | 46 | 869 | 271 |
| 2A | Baseline + water to FT | 9.2 | 54 | 695 | 282 |

It can be seen that by allowing a nominal quantity (9.2 volume percent) of water to enter the F-T reactor, the yield of $CO_2$ increases by about 17 percent. The yield of diesel decreases by 20 percent, and power production increases by 4 percent, mainly because of the additional hydrogen produced by moving the water-gas shift equilibrium to the right.

Example 3

Maximum Hydrocarbons

In the flow sheet of FIG. 4, the yield of liquid hydrocarbons is maximized with two modifications from the flow sheet of FIG. 2. First, waxes 46 produced by the F-T reactor are hydrocracked to lighter hydrocarbon fractions. Second, a substantial fraction (95 percent) of the F-T tail gas 90 (mainly $H_2$, $CO_2$ and $N_2$) is recycled to the gasifier. This large recycle rate is only feasible if $CO_2$ is first removed from the recycle gas; otherwise excessive carbon would be fed to the gasifier. In this example, power production is 66 Mwe, liquid hydrocarbon production is 6365 bbl/day and $CO_2$ production is 47 MMSCFD. Note that the $CO_2$ production is the same as in that of Example 2, and that it cannot be adjusted downward without sacrificing hydrocarbon yield. However, the recycle rate and/or size of the F-T plant can be reduced to decrease the F-T product yield and increase power as needed. Table 2 below summarizes the power production, $CO_2$ yield and hydrocarbon yield from Examples 1–3:

TABLE 2

| Example | | power (MWe) | $CO_2$ (MMSCFD) | hydrocarbons (bbl/day) |
|---|---|---|---|---|
| 1A | Max power, no FT | 330 | 0 | 0 |
| 1 | Max power with FT | 271 | 0 | 869 |
| 2 | Max $CO_2$ | 271 | 46 | 869 |
| 2A | Max $CO_2$ via $H_2O$ to FT | 282 | 54 | 695 |
| 3 | Max hydrocarbons | 66 | 46 | 6365 |

Plant Daily Revenues

Figure 5:
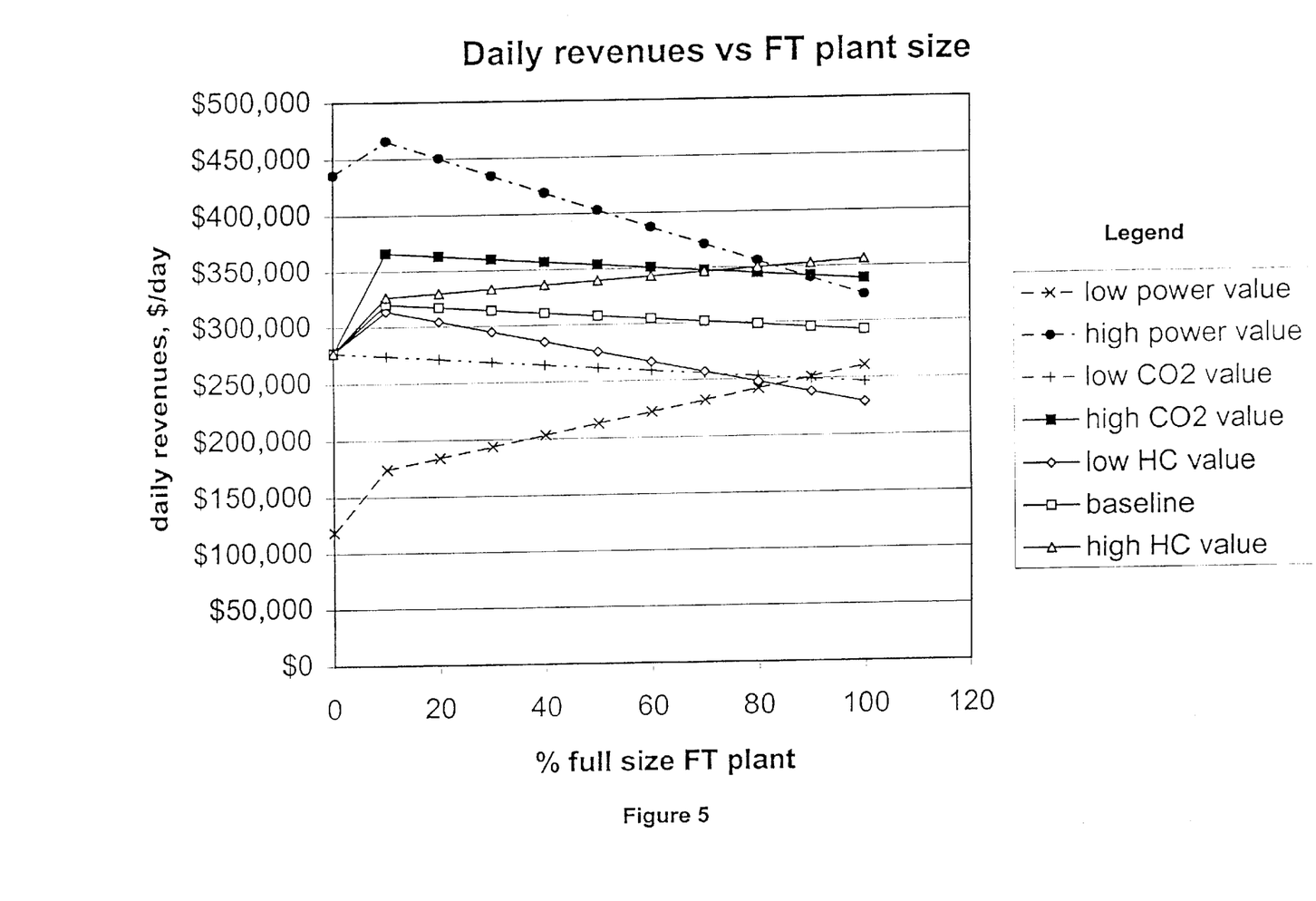
FIG. 5 is a graph of daily revenues vs. F-T plant size, providing an economic analysis of the effects of different process configurations.

The ability of the present invention to maximize actual plant revenues is demonstrated in the graph of FIG. 5. The plant configuration of FIG. 4 was used to estimate daily revenues as a function of the size of the F-T plant. In Example 3, the F-T plant is considered full size, or 100 percent, to maximize hydrocarbon yields. Smaller F-T plants produce less hydrocarbons and more power, but about the same amount of $CO_2$. It was assumed that if no F-T plant is used, (0 percent F-T plant size) the system degenerates to that of FIG. 2 and no $CO_2$ production. In FIG. 5, the values of the power, $CO_2$ and hydrocarbons were varied. A baseline case assumes a power value of 3.5 cents/kilowatt hour, a $CO_2$ value of $1 per thousand cubic feet, and a hydrocarbon value of $30/bbl. In addition to this baseline, six variations were run for the values of the $CO_2$, power and hydrocarbons. The low power value scenario assumes 1.5 cents/kilowatt hour and baseline values for the $CO_2$ and hydrocarbons. The high power value scenario assumes 5.5 cents/kilowatt hour and baseline values for the $CO_2$ and hydrocarbons. The low $CO_2$ value scenario assumes no value for the $CO_2$ and baseline values for the power and hydrocarbons. The high $CO_2$ value scenario assumes $2 per thousand cubic feet of $CO_2$ and baseline values for the power and hydrocarbons. The low hydrocarbon value scenario assumes $20/bbl and baseline values for the power and $CO_2$. The high hydrocarbon value scenario assumes $40/bbl and baseline values for the power and $CO_2$.

Briefly, the graph of FIG. 5 illustrates that in the case of high hydrocarbon value or low power value, maximum plant revenues result from the use of the largest possible F-T plant. In other scenarios, maximum revenues can be obtained with a relatively small F-T plant. For example, in the high power value scenario, revenues are maximized with a 10 percent size F-T plant. A smaller F-T plant gives up the revenues from the $CO_2$ and a larger F-T plant reduces generation of the high value power. In the case of low (zero) $CO_2$ value, the revenues trade off 3.5 cent/kwh power against $30/bbl hydrocarbons. The graph suggests that a smaller F-T plant is appropriate for those values. A slightly lower power value or slightly higher hydrocarbon value would suggest a large F-T plant; i.e., the graph line would slope upwards. It is thus apparent that the partial oxidation—F-T plant—combined cycle plant system of the invention can be designed and operated to selectively maximize the production of at least one of the principal outputs—power, $CO_2$ and hydrocarbons—and to maximize plant revenues as appropriate.

Although the present invention has been described with reference to preferred embodiments, numerous modifications and variations can be made and still the result will come within the scope of the invention. No limitation with respect to the specific embodiments disclosed herein is intended or should be inferred.

We claim:

1. A process for producing power, carbon dioxide and hydrocarbons having an average H:C atom ratio of 2 or greater from carbon-bearing feedstocks having an H:C atom ratio of less than 2, comprising the steps of:

a) reacting a carbon-bearing feedstock with an oxidizing gas and steam in a partial oxidation reactor to produce a mixture of gases containing hydrogen, carbon monoxide and carbon dioxide having a molar ratio of $H_2$:CO of greater than 0.6;

b) reacting the mixture of gases containing hydrogen and carbon monoxide in a Fischer-Tropsch synthesis reactor containing a catalyst which catalyzes both hydrocarbon-forming reactions and the water gas shift reaction;

c) condensing the product hydrocarbons from unreacted hydrogen, carbon monoxide and other gases (tail gases);

d) separating the product hydrocarbons into naphtha, diesel and wax fractions;

e) removing at least a portion of carbon dioxide from the tail gases; and f) producing steam from heat recovered from at least said partial oxidation reactor and said Fischer-Tropsch reactor, directing the steam to the steam turbine of a combined cycle plant, and directing at least the tail gases to the gas turbine of said combined cycle plant to produce power, wherein the process is operated to selectively maximize the production of at least one of the products power, Fischer-Tropsch hydrocarbons and carbon dioxide.

2. The process of claim 1 wherein natural gas is introduced to the partial oxidation reactor to supplement the feedstock.

3. The process of claim 1 wherein natural gas is introduced to the gas turbine of said combined cycle plant to increase power production.

4. The process of claim 1 wherein acid gases are removed from the products of the partial oxidation reactor before they are passed to said Fischer-Tropsch reactor.

5. The process of claim 1 wherein hydrogen is separated from the tail gases and directed to at least one of:

a) the Fischer-Tropsch reactor, and b) a hydrocracking reactor where wax products of the process are hydrocracked to form naphtha and diesel fractions.

6. The process of claim 1 wherein at least a portion of the product hydrocarbons are directed to the gas turbine of said combined cycle plant to increase the production of power.

7. The process of claim 1 wherein said Fischer-Tropsch reactor is a slurry reactor.

8. The process of claim 1 wherein said Fischer-Tropsch catalyst is an iron catalyst.

9. The process of claim 8 wherein said catalyst is an unsupported precipitated iron catalyst promoted with copper and potassium.

10. The process of claim 1, wherein the carbon-bearing feedstock is selected from the group consisting of heavy residual oil from an oil refinery, petroleum coke, coal, aqueous emulsions of bitumen, biomass, rubber tires and mixtures thereof.

11. The process of claim 1 wherein the oxidizing gas is oxygen of a purity greater than about 90 volume percent.

12. The process of claim 1, wherein the oxidizing gas is a mixture of gases containing greater than about 20 volume percent oxygen.

13. The process of claim 1, wherein water is removed from the mixture of gases from step (a) before they are reacted in step (b).

\* \* \* \* \*

UNITED STATES PATENT AND TRADEMARK OFFICE
CERTIFICATE OF CORRECTION

PATENT NO. : 6,306,917 B1
DATED : April 6, 2004
INVENTOR(S) : Mark S. Bohn and Charles B. Benham It is certified that error appears in the above-identified patent and that said Letters Patent is hereby corrected as shown below:

<u>Title page,</u>
Item [75], Inventors, "Charles S. Benham" should read -- Charles B. Benham --.

Signed and Sealed this

Twentieth Day of December, 2005

JON W. DUDAS
*Director of the United States Patent and Trademark Office*

UNITED STATES PATENT AND TRADEMARK OFFICE
CERTIFICATE OF CORRECTION

PATENT NO.   : 6,306,917 B1
DATED        : October 23, 2001
INVENTOR(S)  : Mark S. Bohn and Charles B. Benham

It is certified that error appears in the above-identified patent and that said Letters Patent is hereby corrected as shown below:

<u>Title page,</u>
Item [75], Inventors, "Charles S. Benham" should read -- Charles B. Benham --.

This certificate supersedes Certificate of Correction issued December 20, 2005.

Signed and Sealed this

Twenty-first Day of March, 2006

JON W. DUDAS
*Director of the United States Patent and Trademark Office*